United States Patent
Salamone

(10) Patent No.: US 7,875,661 B2
(45) Date of Patent: Jan. 25, 2011

(54) ORDERED POLYMER SYSTEM AND INTRAOCULAR LENS

(75) Inventor: Joseph C. Salamone, Boca Raton, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 231 days.

(21) Appl. No.: 11/954,090

(22) Filed: Dec. 11, 2007

(65) Prior Publication Data

US 2008/0140193 A1 Jun. 12, 2008

Related U.S. Application Data

(60) Provisional application No. 60/869,611, filed on Dec. 12, 2006.

(51) Int. Cl.
| | |
|---|---|
| *A61F 2/16* | (2006.01) |
| *C08L 29/00* | (2006.01) |
| *C08L 33/24* | (2006.01) |
| *C08L 33/02* | (2006.01) |
| *G02B 1/04* | (2006.01) |

(52) U.S. Cl. .............. 523/106; 623/6.11; 623/6.16; 623/6.59; 623/6.56; 525/219; 525/218; 525/221; 525/199; 525/200

(58) Field of Classification Search ............. 525/218, 525/219, 221, 199, 200; 623/6.11, 6.16, 623/6.56, 6.59; 523/106

See application file for complete search history.

(56) References Cited

U.S. PATENT DOCUMENTS

| | | | |
|---|---|---|---|
| 3,036,985 A | 5/1962 | Daudt et al. | |
| 4,822,360 A * | 4/1989 | Deacon | 623/6.13 |
| 5,236,970 A | 8/1993 | Christ et al. | |
| 5,278,258 A | 1/1994 | Gerace et al. | |
| 5,391,590 A | 2/1995 | Gerace et al. | |
| 5,411,553 A | 5/1995 | Gerace et al. | |
| 5,476,515 A | 12/1995 | Kelman et al. | |
| 6,180,687 B1 | 1/2001 | Hammer et al. | |
| 6,613,343 B2 | 9/2003 | Dillingham et al. | |
| 6,737,496 B2 | 5/2004 | Hodd et al. | |
| 6,815,074 B2 * | 11/2004 | Aguado et al. | 428/447 |
| 7,329,415 B2 * | 2/2008 | Lally et al. | 424/429 |
| 2002/0091175 A1 * | 7/2002 | Sulc et al. | 523/106 |
| 2002/0107337 A1 * | 8/2002 | Rosenzweig et al. | 525/474 |
| 2005/0118270 A1 * | 6/2005 | Moro et al. | 424/485 |
| 2005/0287111 A1 * | 12/2005 | Schlenoff et al. | 424/78.3 |
| 2006/0252850 A1 | 11/2006 | Jani et al. | |
| 2007/0026037 A1 * | 2/2007 | Kloke et al. | 424/423 |

FOREIGN PATENT DOCUMENTS

EP 0968727 A1 1/2000

OTHER PUBLICATIONS

PCT/US2007/085851, "International Search Report and Written Opinion," Jun. 27, 2008.

* cited by examiner

*Primary Examiner*—Vasu Jagannathan
*Assistant Examiner*—Irina Krylova
(74) *Attorney, Agent, or Firm*—Joseph Barrera

(57) ABSTRACT

An intraocular lens with an ordered polymer system contained within a lens capsule or a membrane in the lens capsule. The ordered polymer system includes at least one negatively charged copolymer comprising hydrophilic groups, anionic groups and hydrophobic groups, and at least one positively charged copolymer comprising hydrophilic groups, cationic groups and hydrophobic groups. The at least one negatively charged copolymer and the at least one positively charged copolymer are associatively arranged through non-covalent interactions in the lens capsule or the membrane.

29 Claims, 1 Drawing Sheet

ORDERED POLYMER SYSTEM AND INTRAOCULAR LENS

CROSS-REFERENCE

This application claims the benefit of Provisional Patent Application No. 60/869,611 filed Dec. 12, 2006.

FIELD OF THE INVENTION

The invention relates to an intraocular lens and to materials useful in making intraocular lenses (IOLs).

BACKGROUND OF THE INVENTION

The human eye is a complex sensory organ composed of a cornea, which refracts light on route to the pupil, an iris which controls the size of the pupil thus regulating the amount of light entering the eye, and a lens which focuses the incoming light through the vitreous fluid to the retina. The retina converts the incoming light into electrical energy that is transmitted through the brain stem to the occipital cortex resulting in a visual image.

As the body ages, the effects of oxidative damage contributes to a loss of lens flexibility and the accumulation of denatured proteins that slowly coagulate reducing lens transparency. The natural flexibility of the lens is essential for focusing light onto the retina by a process referred to as accommodation. Accommodation allows the eye to automatically adjust the field of vision for objects at different distances. In general, most accommodation is lost by the age of 50, and this condition is known as presbyopia. Presbyopia usually begins to occur in adults during their mid-forties and mild forms can be treated with glasses or contact lenses.

Lenticular cataract is a lens disorder resulting from the development of coagulated protein and calcification. There are four common types of cataracts: senile cataracts associated with aging, traumatic cataracts which develop after a foreign body enters the lens capsule or following intense exposure to ionizing radiation or infrared rays, complicated cataracts which are secondary to diseases such as diabetes mellitus or eye disorders such as detached retinas, glaucoma and retinitis pigmentosa, and toxic cataracts resulting from medicinal or chemical toxicity. Regardless of the cause, the disease results in impaired vision and may lead to blindness.

Treatment of severe lens disease often requires the surgical removal of the natural lens. Modern surgery involves phacoemulsification, followed by irrigation and aspiration, which removes the lens cortex and nucleus while leaving the lens capsule. An artificial intraocular lens is then inserted into the lens capsule or the anterior chamber to restore vision. Present IOLs have elastomeric characteristics and are designed for small incision implantation. The lenses are typically rolled or folded, inserted into the lens capsule and then unfolded once inside.

To reduce surgical incisions to 1.5 mm or less, some scientists have looked to the development of injectable IOLs in which a polymer lens composition is injected into an empty lens capsule and cured in-situ as a part of the surgical procedure. Essentially, the cured lens will assume the shape of the lens capsule. Alternatively, it has been proposed that one can insert a thin-walled inflatable balloon of silicone rubber into an empty lens capsule. The lens composition is then injected into the balloon and assumes the pre-determined shape of the balloon, presumably to provide greater shape control and containment of the lens composition.

There have been several attempts to develop materials suitable for use as injectable IOLs. For example, Gerace et al. describe a fast curing mixture of vinyl-containing polyorganosiloxane, organosilicone comprising hydride groups and a platinum group metal catalyst in U.S. Pat. Nos. 5,278,258, 5,391,590 ('590) and U.S. Pat. No. 5,411,553. See also, U.S. Pat. Nos. 6,613,343 and 6,737,496 to Hodd et al.

Kelman describes an injectable collagen material in U.S. Pat. No. 5,476,515. The material is said to be clear, resistant to epithelialation and capable of accommodation. The material is prepared from a transparent collagen compound that has a refractive index range from 1.2 to 1.6. The collagen compound is injected into an empty lens capsule.

SUMMARY OF THE INVENTION

The compositions of this invention are designed to mimic the biological materials of the natural lens and the ability of a young natural lens to accommodate, that is, focus on objects at a distance as well as for reading. The compositions comprise an ordered polymer system that is sensitive to shear forces produced by the mechanical contraction and relaxation of the cillary muscles. As a result, the ordered polymer system behaves much like the natural lens material, that is, the intraocular lens exhibits some degree of accommodation.

The invention is directed to an intraocular lens comprising an ordered polymer system contained within a lens capsule or a membrane in the lens capsule. The ordered polymer system comprises at least one negatively charged copolymer comprising hydrophilic groups, anionic groups and hydrophobic groups, and at least one positively charged copolymer comprising hydrophilic groups, cationic groups and hydrophobic groups. The at least one negatively charged copolymer and the at least one positively charged copolymer are associatively arranged through non-covalent interactions in the lens capsule or the membrane.

The invention is also directed to a method of forming the above described intraocular lens. The method comprises: providing at least one negatively charged copolymer comprising hydrophilic groups, anionic groups and hydrophobic groups, and at least one positively charged copolymer comprising hydrophilic groups, cationic groups and hydrophobic groups, removing the natural lens from the lens capsule; and injecting the at least one negatively charged copolymer and the at least one positively charged copolymer into the lens capsule or the membrane positioned in the lens capsule.

The invention is also directed to an intraocular lens in which the ordered polymer system comprises at least one positively charged polyelectrolyte and at least one negatively charged polyelectrolyte with each of the polyelectrolytes having on average at least one ionic group for every four to sixteen carbon atoms along the copolymer backbone.

The invention is also directed to a method of forming the above intraocular lens. The method comprises: providing at least one positively charged polyelectrolyte and at least one negatively charged polyelectrolyte with each of the polyelectrolytes having on average at least one ionic group for every four to sixteen carbon atoms along the copolymer backbone; removing the natural lens form the lens capsule; and injecting the at least one negatively charged polyelectrolyte and the at least one positively charged polyelectrolyte into the lens capsule or the membrane positioned in the lens capsule.

DETAILED DESCRIPTION OF THE INVENTION

Most present day IOLs are made of elastomeric acrylic or silicone materials and are designed for small incision implantation. The lenses are typically rolled or folded, inserted into an empty lens capsule and then unfolded once inside. Unfortunately, most commercially available IOLs are of fixed focus and are not capable of accommodation. Consequently, implantation of such a lens requires the patient to use some form of corrective vision, e.g., reading glasses. Also, the lenses cannot correct the problems associated with presbyopia.

The invention is directed to an intraocular lens composition and an intraocular lens (IOL). The IOL is best described as an ordered polymer (hydrogel) system positioned in an empty lens capsule or a membrane in the lens capsule. The IOL should also exhibit come degree of accommodation. In one embodiment, the ordered polymer system comprises a mixture of two or more amphiphilic copolymers of opposite ionic charge. At least two of these copolymers each comprise hydrophilic groups, ionic groups and hydrophobic groups. The presence of such groups in the copolymers leads to interchain non-covalent interactions, similar to what takes place in the natural lens. For example, hydrophobic interactions can occur through long chain side chains of methylene ($-CH_2-$) or the corresponding fluorinated systems, i.e., ($-CF_2-$). Ionic interactions can occur through pendant anionic and pendant cationic groups. The amphiphilic/ionic copolymers (of opposite charge) will rapidly associate in an aqueous medium. An ordered polymer system results as the oppositely charged ionic groups of the at least two copolymers interact with each other, displacing low molecular weight ions, e.g., sodium chloride. This close ionic interaction of oppositely charged polyions facilitates the hydrophobic interactions between the hydrophobic groups on the oppositely charged copolymers, yielding a gel that is comprised of the at least two interacting copolymer systems.

Figure 1A:
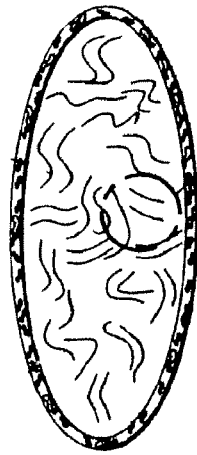
FIG. 1 is a schematic representation of an ordered polymer system that forms within a lens capsule.
Figure 1B:
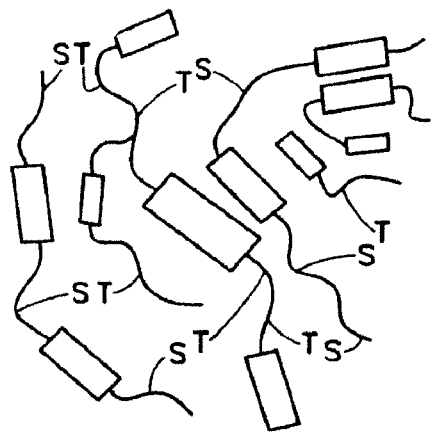

FIG. 1 is a schematic representation of an ordered polymer system that forms within a lens capsule. It is understood by one of ordinary skill in the art that the copolymers used in the ordered polymer system can also be positioned into a membrane that is inserted into an empty lens capsule.

The hydrophilic portion of the at least two copolymers is also important because the copolymers need to have some degree of water solubility which allows the copolymer mixture to form an ordered arrangement of the hydrophobic and ionic side chains, and thereby form the complex gel. The resulting gel is of sufficient elasticity such that it can be deformed by the shear forces produced by the contraction and relaxation of the cillary muscles, and thereby provide for lens accommodation.

The ordered polymer system comprises at least two copolymers with at least one of the copolymers comprising a pendant anionic group S, and at least one copolymer comprising a pendant cationic group T. Each of the at least two copolymers will also comprise pendant hydrophilic groups. These two copolymers are represented by formulae I and II below.

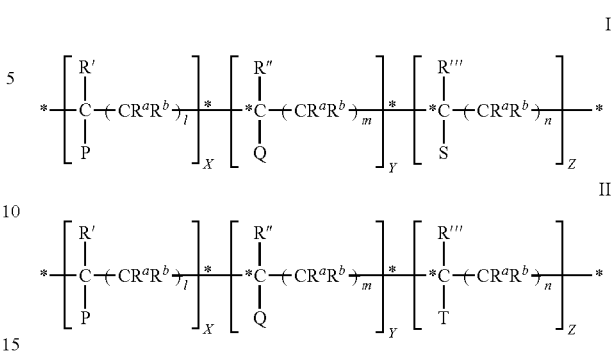

wherein P is a pendant hydrophilic group; Q is a pendant hydrophobic group; S is a pendant anionic group; and T is a pendant cationic group; R', R'', and R''' are independently selected from hydrogen, fluorine, a $C_{1-3}$ alkyl or $-(CH_2)_k$-phenyl (k is 0, 1, 2 or 3); each of $R^a$ and $R^b$ is independently selected from hydrogen, fluorine or methyl; and 1, m and n are integers from 1 to 6; and X, Y and Z are integers from 1 to 100.

Exemplary hydrophilic P groups include, but are not limited to, hydroxymethyl groups, hydroxyethyl groups, ethoxy hydroxyethyl groups, methoxy groups, amide groups, glyceryl groups, urea and thiourea groups, hydroxy groups, formamide groups, sulfone groups, and pyrrolidone groups. Representative monomers include 2-hydroxyethyl(meth)acrylate, glyceryl(meth)acrylate, N-[tris(hydroxymethyl)methyl]-acrylamide, poly(ethylene glycol monomethacrylate), poly(ethylene glycol monomethylether monomethacrylate), acrylamide, N,N-dimethylacrylamide, diacetone acrylamide, N-vinylformamide, N-vinylurea, N-vinylthiourea, vinyl methyl sulfone, vinyl alcohol (from hydrolyzed vinyl acetate), vinyl methyl ether, and N-vinylpyrrolidone.

Exemplary hydrophobic Q groups include, but are not limited to, $C_3$-$C_{18}$ alkyl groups, $C_6$-$C_{30}$ aryl groups, $C_7$-$C_{30}$ arylalkyl groups and fluorinated derivatives thereof. Representative monomers include n-butyl(meth)acrylate, isooctyl(meth)acrylate, n-dodecyl(meth)acrylate, n-hexadecyl(meth)acrylate, benzyl(meth)acrylate, styrene, pentafluorostyrene, vinylnaphthalene, 2-naphthyl(meth)acrylate, m/p-vinylbenzylchloride, m/p-vinylbenzyl bromide, 6-hydroxyhexyl methacrylate, 2-phenylethyl(meth)acrylate, 1,1,1,3,3,3-hexafluoroisopropyl methacrylate, vinyl octadecyl ether, vinyl stearate, vinyl benzoate, 2,2,2-trifluoroethyl methacrylate, 2,2,3,3,3-pentafluoropropyl methacrylate, 2,2,3,3-tetrafluoropropyl(meth)acrylate, 2,2,3,3,4,4,4-heptafluorobutyl acrylate, 2,2,3,3,4,4,5,5,6,6,7,7-dodecafluoroheptyl acrylate, 3,3,4,4,5,5,6,6,7,7,8,8,9,9,10,10-heptadecafluorodecyl methacrylate, and 2,3,3,4,4,5,5-octafluoropentyl methacrylate.

Exemplary anionic S groups include, but are not limited to, carboxylic acids, sulfonic acids, sulfuric acids, sulfinic acids, phosphoric acids, phosphonic acids, and phosphinic acids. Representative monomers include acrylic acid, methacrylic acid, styrenecarboxylic acid, maleic acid, fumaric acid, itaconic acid, 2-acrylamidoglycolic acid, vinylsulfonic acid, 2-acrylamido-2-methyl-1-propanesulfonic acid, 2-methacryloyloxyethylsulfonic acid, 2-methacryloyloxyethylsulfuric acid, styrenesulfonic acid, vinylphosphonic acid, vinylsulfonic acid, styrenephosphonic acid, 2-methacryloyloxyethylphosphonic acid, 2-methacryloyloxypropylphosphoric acid, and 3-methacrylamidopropylphosphonic acid, in either their acid form or salt form. If the free acid is used, and the anionic copolymer is mixed with the cationic copolymer, a low molecular weight acid, such as hydrochloric acid, is generated. However, if the acid polymer is in its salt form, such as its sodium salt, the low molecular compound released is sodium chloride. Thus, it is preferable that the polyanion be in its salt form if the polycation is in its salt form.

Exemplary cationic T groups include, but not limited to, primary, secondary, tertiary, and quaternary amino groups, sulfonium groups, guanidinium groups, and phosphonium groups. The preferred functional groups include tertiary amino groups and quaternary ammonium groups. Representative monomers include 3-acrylamidopropyltrimethylammonium chloride, 2-methacryloyloxyethyl-N,N-dimethylamine, 2-methacryloyloxyethyl-N,N,N-trimethylammonium chloride, vinylbenzylamine, p-aminostyrene, vinylpyridine, vinylpyridinium salts, vinylimidazole, vinylimidazolium salts, vinyltriazole, vinyltriazolium salts, 2-methacryloyloxyethylamine hydrochloride, methacryloyloxyethyldiphenylsulfonium chloride, N-vinylguanidinium chloride, p-vinylbenzyltriphenylphosphonium chloride. It should be noted that many other salt anions can be used, such as bromide, iodide, methylsulfate, toluenesulfate, and the like. For similar reasons noted above, it is preferred that the polycation be in its salt form for interacting with the polyanion in its salt form. However, if the free acid of a polyanion, e.g., a polyacid, interacts with either a primary, secondary, or tertiary amine, protonation of the polymeric amine will occur. As a result, the acid containing polymer will then be in its salt form, i.e., a polyanion, and a polyelectrolyte complex will result without the removal of any low molecular weight electrolyte.

Each of the respective copolymers can be obtained by free radical polymerization. For example, the cationic copolymer is prepared by copolymerizing a cationic monomer such as 3-methacrylamidopropyltrimethylammonium chloride, a neutral monomer such as N,N-dimethylacrylamide and an a hydrophobic monomer such as 2,2,3,3,4,4,5,5,6,6,7,7-dodecafluoroheptyl acrylate. The mol % of each of these monomers are present in the cationic copolymer as follows: from 5 mol % to 50 mol %, preferably from 10 mol % to 25 mol %, of the cationic monomer; from 50 mol % to 95 mol %, preferably from 48 mol % to 90 mole %, of the neutral monomer; and from 0.001 mol % to 5 mol %, preferably from 0.01 mol % to 2.0 mole %, of the hydrophobic monomer. The resulting cationic copolymer is water soluble and can be purified by either dialysis or precipitation into a non-solvent.

Similarly, the anionic copolymer can be prepared from an anionic monomer such as sodium styrenesulfonate, a neutral monomer such as N,N-dimethylacrylamide, and a hydrophobic monomer such as 2,2,3,3,4,4,5,5,6,6,7,7-dodecafluoroheptyl acrylate. The mol % of each of the monomers are present in the anionic copolymer as follows: from 5 mol % to 50 mol %, preferably from 10 mol % to 25 mol %, of the anionic monomer; from 50 mol % to 95 mol %, preferably from 48 mol % to 90 mole %, of the neutral monomer; and from 0.001 mol % to 5 mol %, preferably from 0.01 mol % to 2.0 mol %, of the hydrophobic monomer. The resulting anionic copolymer is water soluble and can be purified by either dialysis or precipitation into a non-solvent.

In a preferred embodiment, the mol % of cationic monomer and the mol % of anionic monomer in each of the respective copolymers will be within 10 mol % of each other, more preferably within 5 mol % of each other, and most preferably equivalent to each other. As a result, the concentration of oppositely charged groups will be equivalent, or at least nearly equivalent, in the ordered polymer system.

In other words, the at least one copolymer with pendant anionic groups and the at least one copolymer with pendant cationic groups are present in select proportions to provide a charge ratio of from 4:1 to 1:4, from 2:1 to 1:2, from 1.2:1 to 1:1.2 and preferably in a ratio of about 1:1. For example, the total number of charged groups of copolymer having anionic groups to the total number of charged groups of copolymers having cationic groups is from 4:1 to 1:4 or from 2:1 to 1:2. Preferably, the charge ratio is from 1.2:1 to 1:1.2, with a charge equivalence of about 1:1 being most preferred.

As the two oppositely charge copolymers are mixed in an aqueous solution, a clear gel is formed. The strength of the gel is determined by the charge density of the oppositely charged ionic groups and the amount of hydrophobic groups. Because little, or no, covalent bonds are formed and most, if not all, of the polymer interactions are deformable by high shear, the gel is shear sensitive and is particularly suited as an injectable lens composition. Once the gel is at rest, the ordered polymer structure will form, resulting in a stabilized gel. Through the low deformation shear forces provided by the cillary muscles, the stabilized gel can function as an accommodating lens.

The refractive index of the resulting gel can be increased by using monomers with aromatic substituents. For example, one can use the hydrophobic monomer, 2-phenylethyl (meth) acrylate. Alternatively, the refractive index can be increased by careful selection of the cationic and anionic monomers such as p-vinylbenzyltrimethylammonium chloride and sodium p-styrenesulfonate, respectively.

UV blocking agents can also be included in the lens compositions at a concentration from 0.2 wt % to 4 wt %. For example, the UV absorbing monomers, 2-(2'-methacryloyloxy-5'-methylphenyl)benzotriazole and like compounds, can be used. This and other UV blocking agents are described in U.S. patent application Ser. No. 11/122,180 filed May 4, 2005.

In another embodiment, the ordered polymer system comprises one or more polyelectrolytes, which are generally high molecular weight polymers with multiple anionic or cationic functional groups. The polyelectrolyte polymer system comprises at least one polyelectrolyte polymer with side chains that include cationic groups, and at least one polyelectrolyte polymer with side chains that include anionic groups. In spite of the side chains with the cationic and anionic groups, it is preferred that the resulting ordered polyelectrolyte complex polymer system is an overall neutral or near-neutral polymer system (the mole ratio of cationic groups to anionic groups is from 2:1 to 1:2, and preferably 1:1). It is believed that multiple ionic points in the ordered polymer system facilitate the ordering of polyelectrolyte polymers, which leads to relatively fast set or gel times.

The organic polyelectrolyte copolymers should have a sufficient high molecular weight (preferably at least 10,000) and contain a plurality of ionic groups (anionic or cationic). The polyelectrolyte copolymers will have on average at least one such ionic group for every four to sixteen carbon atoms along the copolymer backbone. For example, a polyelectrolyte copolymer will have one such ionic group for every six repeating monomeric units of the copolymer chain.

Solutions of the polyelectrolyte copolymers are prepared in conjunction with a binary solvent such as water and salt, or a ternary solvent such as water, salt and an organic cosolvent. The solvent system is typically a low molecular weight electrolyte, e.g., saline. A water-soluble organic cosolvent may be necessary if one or more aromatic- or fluorocarbon-based polyelectrolyte copolymers are used.

Following injection of the polyelectrolyte solutions into the lens capsule, the low molecular weight electrolyte will diffuse through the lens capsule. The resulting decrease in ionic shielding of the oppositely charged polyions as the low molecular weight electrolyte diffuses out of the capsule leads to gel formation. The resulting ordered polymer system behaves as an ionically crosslinked polymer, further interlocked with hydrophobic interactions, with hydrogel characteristics.

The polyelectrolyte polymers will also be ordered, that is, stabilized by a phenomenon known as chain entanglement between the different polyelectrolyte polymers of the same or different charge. As a result, the ordered polymer system is anchored by the ionic interactions, the hydrophobic interactions, and the chain entanglement between the different polyelectrolyte polymers.

Another preferred example of the formation of ordered polyelectrolyte system is through the interaction of traditionally hydrophilic polymers, without the presence of an added hydrophobic component. For example, naturally occurring polypeptides such as poly(glutamic acid) can be mixed with polylysine, or polysaccharides such as cationic chitosan hydrochloride can be mixed with sodium hyaluronate, to generate ordered polyelectrolyte systems derived from natural sources. Similar phenomena can occur with synthetic polyelectrolytes in the absence of a hydrophobic comonomer provided that suitable monomers are selected.

The polyelectrolyte polymers can be linear, branched, or crosslinked polymers or copolymers. If naturally occurring polyelectrolytes are utilized, the polymers could also have stereoregularity and chirality. The molecular weight of polyelectrolytes should be between 20,000 Daltons and 1,000,000 Daltons, with higher molecular weights, for example, between 75,000 and 500,000 Daltons being preferred, to enhance the stability of the ordered polymer system through increased chain entanglement or the plurality of ionic anchors.

The ordered polymer systems described above and the methods of forming the ordered polymer systems provide IOLs that can accommodate. The ordered polymer system is designed to be used as an injectable IOL material, or IOLs that are partially formed with an injectable IOL material. As a result, the copolymers of the lens composition should have a viscosity less than 60,000 cSt, and more preferably, the viscosity should be less than 8000 cSt. Also, the lens composition prior to setting (gelling) should have a specific gravity from 1.03 to 1.20.

The resulting ordered polymer systems that form in the lens capsule will have a refractive index from 1.38 to 1.65, 1.38 to 1.55 or 1.38 to 1.48. The refractive index of the ordered polymer systems can be increased by the careful selection and design of the copolymers. The refractive index can also be increased by careful selection of the ionic monomers in the copolymers, e.g., by increasing the content of ionic monomers such as p-styrenesulfonic acid, or its corresponding salt, or p-trimethylaminostyrene salt. Alternatively, the refractive index of the ordered polymer system can be increased by using hydrophobic, neutral aromatic containing monomers such as 2-phenylethyl acrylate and 2-phenylethyl methacrylate.

Figure 2A:
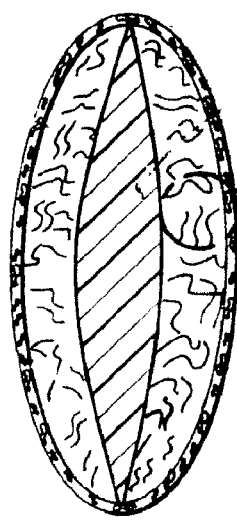
FIG. 2 is a schematic representation of an ordered polymer system in combination with an IOL substrate material within a lens capsule.
Figure 2B:
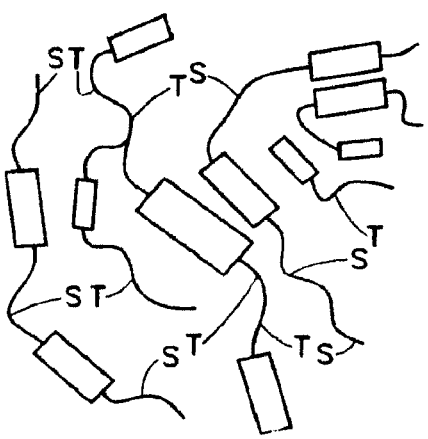

The copolymers described above can also be used as a stabilized coating of sort in combination with known intraocular (IOL) substrate materials, that is, silicone-based IOL's, hydrogels or acrylic-based IOL materials. FIG. 2 is a schematic representation of an IOL comprising an IOL substrate material and an ordered polymer system within a lens capsule.

In one embodiment, the known IOL substrate materials have been surface-modified, which facilitates the formation of a stable interface layer with an interface polymer system or the ordered polymer system. The IOL material can be selected from a range of shapes and sizes according to the individual optic corrections required for each patient. The IOL material acts as a support for the ordered polymer system. Essentially, the IOL will comprise a substrate IOL material, e.g., a surface modified poly(2-phenylethyl acrylate-co-2-phenylethyl methacrylate)) or a silicone-based IOL, and the ordered polymer system, and optionally an interface forming polymer. The surface modification could include a charge such that an oppositely charged polyion will first ionically bond to the surface followed by interaction with its polymeric counterpart of opposite charge.

In one embodiment, the IOL substrate material is inserted into an empty lens capsule bag using methods well known to those of ordinary skill in the art. Typically, the IOL substrate material is inserted into a small incision with any IOL insertion device known in the art. Once properly inserted in the lens capsule the ordered polymer system is injected into the capsule. The ordered polymer system polymer flows around the IOL material and covalently attaches, or is non-covalently secured, e.g., by hydrogen bonding interactions or van der Waals interactions, to the IOL material. The ordered polymer system is then provided sufficient time to gel.

One advantage of using an IOL substrate material in combination with the ordered polymer system is that the physical size of the IOL material is significantly smaller than if the IOL material alone was relied upon for the requisite refractive power of the lens. As a result, the incision size required for insertion of the IOL substrate material is smaller. A lens of thinner cross section is more flexible and can be rolled or folded to a smaller cross section, and hence, can be inserted through an incision size of 1.6 mm or less, preferably inserted through an incision size from 0.8 mm to 1.4 mm.

In another embodiment, the IOL substrate material is inserted into an empty lens capsule using methods well known to those of ordinary skill in the art. Typically, the IOL substrate material is inserted into a small incision with any IOL insertion device known in the art. Once properly inserted and positioned in the lens capsule, an interface forming polymer is injected into the capsular. The interface forming polymer flows around the IOL substrate material and covalently attaches, or is non-covalently secured, to the IOL substrate material. Any excess interface forming polymer can be removed, e.g., by flushing with saline, through the small incision.

The interface layer can be covalently attached to the surface of the IOL substrate material. Preferably, the IOL substrate material will have a surface that has been modified to include surface functionality that can chemically react with select functional groups in the interface forming polymer. For example, plasma treatment methods known to those of ordinary skill in the art can be used to provide acidic (anionic) functionality to a surface of known IOL materials. In some cases the, the IOL can be surface-modified by the use of covalent coatings that provide acidic functionality to the surface. Preferably, the covalent coatings will also provide some lubricious character to the surface of the IOL which will facilitate insertion and positioning of the IOL substrate in the lens capsule.

The interface forming polymer can include select functional groups, e.g., epoxy groups or other like groups, which can react with the acidic groups of the plasma-modified surface or the covalent coating, thereby forming the interface layer. The interface forming polymer will also include ionic and/or hydrophobic side chains that will react with or become entangled with the ordered polymer system. Preferably, the interface forming polymer is hydrophilic.

Once the interface layer forms about the interface forming polymer, the ordered polymer system is injected into the lens capsule. The copolymers flow around the IOL material with the interface layer and covalently attaches, or is non-covalently secured, to the interface layer. Essentially, non-covalent and/or covalent interactions are formed between the interface layer and the copolymers of the ordered polymer system. The ordered polymer system is then provided sufficient time to gel.

IOL Substrate Materials

The IOL substrate materials are IOL materials that are capable of being folded in an insertion device and which can regain the shape of a lens following insertion into an empty lens capsule. Any IOL substrate material known in the art can be used in combination with the ordered polymer system to form an IOL lens. Exemplary IOL substrate materials are described below.

One IOL substrate material is prepared from at least three constituents. The first constituent, preferably present in a major amount (at least about modified 50 wt %), is a first monomeric component, the homopolymers of which have a refractive index of at least 1.50, preferably at least 1.52 or 1.54. The homopolymers of the first monomeric component preferably have a substantial degree of rigidity. The second constituent, preferably present in at least 3 wt %, 10 wt % or 20 wt %, is a second monomeric component, the homopolymers of which have a glass transition temperature of less than 30° C., preferably less than 22° C. The stated weight percents (wt %) are in reference to the total weight of polymer or polymer additive constituents used to manufacture the IOL substrate material, and thereby excludes any reaction solvent or extractables not present in the final IOL material.

As used herein, the term "homopolymer" refers to a polymer which is derived substantially completely from the monomeric component in question. As a result, the homopolymer includes as the primary, preferably sole, monomeric component, the monomeric component in question. Minor amounts of catalysts, initiators and the like may be included, as is conventionally the case, in order to facilitate the formation of the homopolymer.

The first and second constituents together are preferably present in at least 80 wt %, more preferably at least 90 wt %. The first and second monomeric components are preferably selected so that each of these monomeric components can chemically react with the other monomeric component.

Particularly useful first monomeric components include styrene,

N-vinylcarbazole, vinylnaphthalene, benzyl methacrylate, phenyl methacrylate, 2-phenylethyl methacrylate, naphthyl methacrylate, pentabromophenyl acrylate, 2-phenoxyethyl methacrylate, 2,3-dibromopropyl acrylate and mixtures thereof. Particularly useful second monomeric components include n-butyl acrylate, 2-phenoxyethyl acrylate, n-hexyl acrylate, 2-ethylhexyl acrylate, 2-ethoxyethyl acrylate, 2,3-dibromopropyl acrylate, n-1,1-dihydroperfluorobutyl acrylate and mixtures thereof.

The third constituent is a crosslinking monomeric component, that is, a monomeric component that can cross link with the first or the second monomeric components. The crosslinking monomeric component is preferably multi-functional and can chemically react with both the first and second monomeric components. The crosslinking monomeric component is preferably present in less than 1 wt %. Examples of useful crosslinking monomeric components include ethylene glycol dimethacrylate, propylene glycol dimethacrylate, ethylene glycol diacrylate and the like and mixtures thereof.

In a preferred embodiment, the first monomeric component will include one or more aryl-containing groups. It is believed that the presence of such aryl-containing groups in the first monomeric component at least facilitates, and preferably leads to or results in, the present copolymers having a desirable high refractive index. If the first monomeric component includes one or more aryl-containing groups, it is preferred that the second monomeric component does not include aryl-containing groups. The use of only one of the monomeric components to control or set the refractive index of the IOL material provides flexibility in selecting the other monomeric component or components in order to provide optimal properties, other than refractive index, for insertable/foldable IOLs.

Methods of making the IOL substrate material from the at least three constituents above is described in U.S. Pat. No. 5,331,073 (column 6, lines 11 to 63).

Another IOL substrate material comprises a copolymer formed from the following three different (meth)acrylate monomers:

a perfluorooctylethyloxypropylene(meth)acrylate of formula (AA),

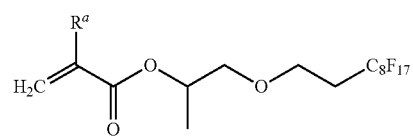

wherein $R^a$ is hydrogen or methyl;

a 2-phenylethyl(meth)acrylate monomer of formula (BB),

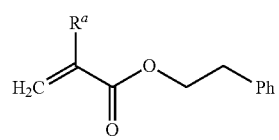

wherein $R^a$ is hydrogen or methyl; and
an alkyl(meth)acrylate monomer of formula (CC),

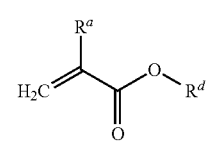

wherein $R^a$ is hydrogen or methyl and $R^d$ is a linear or branched $C_{4-12}$ alkyl group. A crosslinking monomeric component as described above is also used in the preparation of the aryl-(meth)acrylate IOL materials.

The monomer of the formula (AA) can be added in an amount from 5 wt % to 20 wt %, more preferably from 7 wt % to 15 wt %. The monomer formula (BB) can be added in an amount from 40 to 60% by weight, more preferably from 42 wt % to 56 wt %. The monomer of formula (CC) can be added in an amount from 30 wt % to 50 wt %, more preferably 35 wt % to 46 wt %. The amount of the crosslinking monomer is preferably 0.5 wt % to 4 wt %, preferably 1 wt % to 3.5%, based on the total amount of the monomers of formulae (AA), (BB) and (CC).

Methods of making the aryl (meth)acrylate IOL materials above is described in U.S. Pat. No. 5,814,680 (column 5, lines 1 to 51).

Another IOL substrate material comprises a copolymer formed from two or more (meth)acrylate monomers of formula (DD).

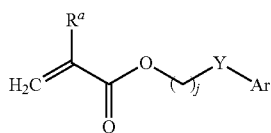

DD wherein: $R^a$ is H or $CH_3$; j is 0-10; Y is nothing, O, S, or NR wherein R is H, $CH_3$, $C_nH_{2n+1}$ (n=1-10), $-OC_3H_7$, $-Ph$, or $-CH_2Ph$ (Ph is phenyl); Ar is any aromatic ring such as phenyl, which can be unsubstituted or substituted with H, F, $CH_3$, $C_2H_5$, n-$C_3H_7$, iso-$C_3H_7$, $-OCH_3$, $-C_6H_{11}$, $-Cl$, $-Br$, $-Ph$ or $-CH_2Ph$; and a cross-linking monomer having a plurality of polymerizable ethylenically unsaturated groups. The polymers have a glass transition temperature not greater than 37° C. and an elongation of at least 150%.

Some of the more exemplary (meth)acrylate monomers used to make the IOL substrate material include, but are not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates.

It will be understood by those skilled in the art, that among polymers of acrylic esters, those made from acrylate ester monomers tend to have lower glass transition temperatures and to be more flexible than polymers of methacrylate esters. Accordingly, the aryl acrylate/methacrylate copolymers used in the substrate IOL materials will generally comprise a greater mole percent of acrylate ester residues than of methacrylate ester residues. It is preferred that the aryl acrylate monomers constitute from 60 mole percent to 95 mole percent of the polymer, while the aryl methacrylate monomers constitute from 5 mole percent to 40 mole percent of the polymer. Most preferred is a polymer comprising 60-70 mole percent 2-phenylethyl acrylate, and 30-40 mole percent 2-phenylethyl methacrylate. Also, the proportions of the monomers should be chosen to produce a copolymer having a glass transition temperature not greater than about 37° C.

Methods of making the arylacrylate IOL materials above is described in U.S. Pat. No. 5,290,892 (column 4, line 37 to column 5, line 22).

Another IOL substrate material comprises a copolymer formed from the following monomeric components: (a) a first monomeric component which is an aryl acrylate or an aryl methacrylate; (b) a second monomeric component which is a monomer having an aromatic ring with a substituent having at least one site of ethylenic unsaturation; and c) a third monomeric component which is a high water content hydrogel-forming monomer. The copolymer further includes a crosslinking agent, and the second monomeric component is not an acrylate The monomeric composition used to make the aryl acrylate IOL materials comprises at least 20 wt % of the first monomeric component such as ethylene glycol phenyl ether acrylate or poly(ethylene glycol phenyl ether acrylate); at least 10 wt % of the second monomeric component such as styrene or substituted styrene; at least 10 wt % of the third monomeric component such as 2-hydroxyethyl methacrylate, hydroxyethoxy ethyl methacrylate, or methacrylic acid; and less than about 10 wt % of a crosslinking agent such as a diacrylate or a dimethacrylate. The resulting copolymer has a refractive index greater than about 1.50 and is foldable at normal room temperature, that is, about 20° C. to 25° C.) when hydrated.

Again, the above IOL substrate materials can be produced using polymerization methods well known to those of ordinary skill in the art.

Another IOL substrate material comprises a reinforced, crosslinked silicone elastomer copolymer comprising 12 to 18 mol % of aryl substituted siloxane units of the formula R4R5-SiO where the aryl substituents (R4 and R5 groups) can be phenyl groups, mono-lower alkyl substituted phenyl groups, or di-lower alkyl substituted phenyl groups, and can be identical with one another or different from one another. Preferably, both aryl groups are unsubstituted phenyl, and the resulting diphenylsiloxane unit is present in the copolymer in a ratio of 14 to 16 mol %.

The silicone elastomer copolymer is further end blocked with trisubstituted (monofunctional) siloxane units, and at least one substituent of the end blocking group contains an olefinic bond (e.g., vinyl). Thus, the formula of the end blocking group incorporated in the copolymer is $R_1R_2R_3-SiO_5$ where the nature of the $R_1$ and $R_2$ is not critical, and can include, for example, alkyl, aryl, or substituted alkyl or substituted aryl groups. $R_1$ and $R_2$ may be the same or different from one another. $R_3$ is an alkenyl group, preferably a vinyl group. In one preferred silicone elastomer copolymer, the end blocking group is a dimethyl, vinyl siloxane unit. The role of the olefinic (vinyl) group, is to enable curing or crosslinking of the copolymer as well as covalently linking, in accordance with another feature, certain ultraviolet light absorbing compounds to the crosslinked copolymer matrix of an intraocular lens.

The silicone elastomer copolymer also contains a trimethylsilyl treated silica reinforcer finely dispersed in the copolymer. The silica reinforcer is used in a ratio of 15 to 45 parts by weight of the reinforcer to 100 parts of the copolymer. The treated silica is commercially available. Alternatively, processes for trimethylsilylating the surface of fume silica for the purpose of rendering the silica surface hydrophobic and compatible with polysiloxane polymers is known and within the skill of the ordinary art. See, U.S. Pat. Nos. 3,341,490 and 3,036,985, which refer to and describe such processes for trimethylsilylating fume silica.

In accordance with the present invention the silica reinforcer used for the composition has a surface area of 100 to 450 m²/g. In a particular embodiment, the silica reinforcer will have a surface area of approximately 200 m²/g, and present in a weight ratio of approximately 27 parts to 100 parts of the copolymer. The intimate mixing is preferably aided by treating the mixture on a roll mill or like device. After intimate mixing, volatiles, such as unreacted silylating agent, gaseous by-products and water are removed from the mixture by heat and vacuum.

Again, the above silicon elastomer copolymer can be produced using polymerization methods well known to those of ordinary skill in the art. Methods of making the silicon elastomer copolymer are described in U.S. Pat. No. 5,236,970 (column 4, line 11 to column 5, line 25).

The copolymers have a suitable viscosity to be injected through standard cannula with an 18 Gauge needle or finer, and therefore they can be injected into an empty lens capsule or a membrane that is positioned in a lens capsule. Accordingly, the copolymers should have a viscosity lower than 60 000 cSt or below 8000 cSt.

The copolymers can be provided in the form of a kit, that is, in separately stored compartments. The kit can also contain a rinse solution to extract portions of the ordered polymer system following a brief period following injection.

We claim:

1. An intraocular lens comprising an ordered polymer system contained within a lens capsule or a membrane in the lens capsule, wherein the ordered polymer system comprises at least one negatively charged copolymer comprising hydrophilic groups, anionic groups and hydrophobic groups, and at least one positively charged copolymer comprising hydrophilic groups, cationic groups and hydrophobic groups, said at least one negatively charged copolymer and said at least one positively charged copolymer associatively arranged through non-covalent interactions in the lens capsule or the membrane resulting in the ordered polymer system, wherein the ordered polymer system is in the form of a gel of sufficient elasticity such that it can be deformed by the shear forces produced by the contraction and relaxation of the cillary muscles, and thereby provide for lens accommodation.

2. The lens of claim 1 wherein the at least one negatively charged copolymer and the at least one positively charged copolymer comprise side chains of methylene or a corresponding fluorinated side chains.

3. The lens of claim 1 wherein the at least one negatively charged copolymer is of formula I

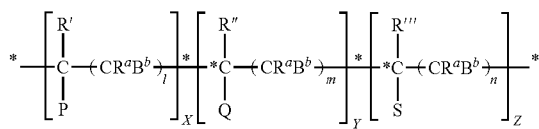

wherein P is a pendant hydrophilic group; Q is a pendant hydrophobic group; and S is a pendant anionic group;

R', R'', and R''' are independently selected from hydrogen, fluorine, a $C_{1-3}$ alkyl or $—(CH_2)_k$-phenyl (k is 0, 1, 2 or 3);

each of $R^a$ and $R^b$ is independently selected from hydrogen, fluorine or methyl;

l, m and n are integers from 1 to 6; and X, Y and Z are integers from 1 to 60.

4. The lens of claim 1 wherein the at least one positively charged copolymer is of formula II

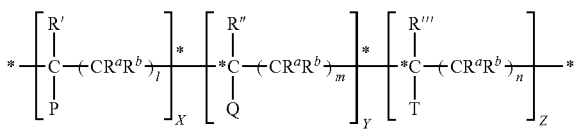

wherein P is a pendant hydrophilic group; Q is a pendant hydrophobic group; and T is a pendant cationic group;

R', R'', and R''' are independently selected from hydrogen, fluorine, a $C_{1-3}$ alkyl or $—(CH_2)_k$-phenyl (k is 0, 1, 2 or 3);

each of $R^a$ and $R^b$ is independently selected from hydrogen, fluorine or methyl;

l, m and n are integers from 1 to 6; and x, y and z are integers from 1 to 60.

5. The lens of claim 1 wherein the at least one positively charged copolymer is prepared with one or more monomers with at least one cationic group selected from the group consisting of primary, secondary, tertiary, and quaternary amino groups, sulfonium groups, guanidinium groups and phosphonium groups, and the corresponding salts thereof.

6. The lens of claim 1 wherein the at least one negatively charged copolymer is prepared with one or more monomers with at least one anionic group selected from the group consisting of carboxylic acids, sulfonic acids, sulfuric acids, sulfinic acids, phosphoric acids, phosphonic acids and phosphinic acids, and the corresponding salts thereof.

7. The lens of claim 1 wherein the at least one positively charged copolymer and the at least one negatively charged copolymer comprise a charge ratio from 2:1 to 1:2.

8. The lens of claim 7 wherein the charge ratio is from 1.2:1 to 1:1.2.

9. The lens of claim 1 further comprising an IOL substrate material that is embedded within the ordered polymer system.

10. An intraocular lens comprising an ordered polymer system contained within a lens capsule or a membrane in the lens capsule, wherein the ordered polymer system comprises at least one positively charged polyelectrolyte and at least one negatively charged polyelectrolyte with each of the polyelectrolytes having on average at least one ionic group for every four to sixteen carbon atoms along the copolymer backbone, said at least one negatively charged copolymer and said at least one positively charged copolymer associatively arranged through non-covalent interactions in the lens capsule or the membrane resulting in the ordered polymer system, wherein the ordered polymer system is in the form of a gel of sufficient elasticity such that it can be deformed by the shear forces produced by the contraction and relaxation of the cillary muscles, and thereby provide for lens accommodation.

11. The lens of claim 10 wherein the at least one positively charged polyelectrolyte is prepared with one or more monomers with at least one cationic group selected from the group consisting of primary, secondary, tertiary, and quaternary amino groups, sulfonium groups, guanidinium groups and phosphonium groups, and the corresponding salts thereof.

12. The lens of claim 10 wherein the at least one negatively charged copolymer is prepared with one or more monomers with at least one anionic group selected from the group consisting of carboxylic acids, sulfonic acids, sulfuric acids, sulfinic acids, phosphoric acids, phosphonic acids and phosphinic acids, and the corresponding salts thereof.

13. The lens of claim 10 wherein the at least one positively charged polyelectrolyte and the at least one negatively charged polyelectrolyte comprise a charge ratio from 2:1 to 1:2.

14. The lens of claim 13 wherein the charge ratio is from 1.2:1 to 1:1.2.

15. The lens of claim 10 further comprising an IOL substrate material that is embedded within the ordered polymer system.

16. A method of forming an intraocular lens in a lens capsule or a membrane positioned in the lens capsule, the method comprising:
providing at least one negatively charged copolymer comprising hydrophilic groups, anionic groups and hydrophobic groups, and at least one positively charged copolymer comprising hydrophilic groups, cationic groups and hydrophobic groups,
removing the natural lens form the lens capsule; and
injecting the at least one negatively charged copolymer and the at least one positively charged copolymer into the lens capsule or the membrane positioned in the lens capsule, resulting in an ordered polymer system, wherein the ordered polymer system is in the form of a gel of sufficient elasticity such that it can be deformed by the shear forces produced by the contraction and relaxation of the cillary muscles, and thereby provide for lens accommodation.

17. The method of claim 16 wherein the at least one negatively charged copolymer is of formula I and the at least one positively charged copolymer is of formula II

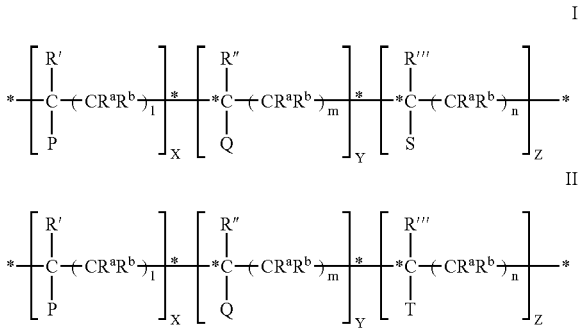

wherein P is a pendant hydrophilic group; Q is a pendant hydrophobic group; and S is a pendant anionic group; T is a pendant cationic group;
R', R", and R''' are independently selected from hydrogen, fluorine, a $C_{1-3}$ alkyl or $—(CH_2)_k$-phenyl (k is 0, 1, 2 or 3);
each of $R^a$ and $R^b$ is independently selected from hydrogen, fluoroine or methyl;
l, m and n are integers from 1 to 6; and x, y and z are integers from 1 to 60.

18. The method of claim 16 wherein the at least one positively charged copolymer and the at least one negatively charged copolymer comprise a charge ratio from 2:1 to 1:2.

19. The method of claim 16 further comprising inserting an IOL substrate material into the lens capsule or into the membrane positioned in the lens capsule.

20. A method of forming an intraocular lens in a lens capsule or a membrane positioned in the lens capsule, the method comprising:
providing at least one positively charged polyelectrolyte and at least one negatively charged polyelectrolyte with each of the polyelectrolytes having on average at least one ionic group for every four to sixteen carbon atoms along the copolymer backbone;
removing the natural lens form the lens capsule; and
injecting the at least one negatively charged polyelectrolyte and the at least one positively charged polyelectrolyte into the lens capsule or the membrane positioned in the lens capsule resulting in an ordered polymer system, wherein the ordered polymer system is in the form of a gel of sufficient elasticity such that it can be deformed by the shear forces produced by the contraction and relaxation of the cillary muscles, and thereby provide for lens accommodation.

21. The method of claim 20 wherein the at least one negatively charged polyelectrolyte is prepared from one or more monomers with at least one anionic group selected from the group consisting of carboxylic acids, sulfonic acids, sulfuric acids, sulfinic acids, phosphoric acids, phosphonic acids and phosphinic acids, and the corresponding salts thereof.

22. The method of claim 20 wherein the at least one positively charged polyelectrolyte is prepared with one or more monomers with at least one cationic group selected from the group consisting of primary, secondary, tertiary, and quaternary amino groups, sulfonium groups, guanidinium groups and phosphonium groups, and the corresponding salts thereof.

23. The method of claim 20 wherein the at least one positively charged polyelectrolyte and the at least one negatively charged polyelectrolyte comprise a charge ratio from 2:1 to 1:2.

24. The method of claim 20 further comprising inserting an IOL substrate material into the lens capsule or into the membrane positioned in the lens capsule.

25. The lens of claim 3 wherein the at least one positively charged copolymer is of formula II

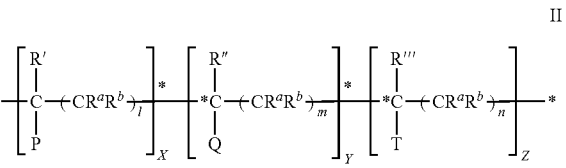

wherein P is a pendant hydrophilic group; Q is a pendant hydrophobic group; and T is a pendant cationic group;
R', R", and R''' are independently selected from hydrogen, fluorine, a $C_{1-3}$ alkyl or $—(CH_2)_k$-phenyl (k is 0, 1, 2 or 3);
each of $R^a$ and $R^b$ is independently selected from hydrogen, fluorine or methyl;
l, m and n are integers from 1 to 6; and x, y and z are integers from 1 to 60.

26. The lens of claim 25 wherein the at least one positively charged copolymer is prepared with one or more monomers with at least one cationic group selected from the group consisting of primary, secondary, tertiary, and quaternary amino groups, sulfonium groups, guanidinium groups and phosphonium groups, and the corresponding salts thereof.

27. The lens of claim 26 wherein the at least one negatively charged copolymer is prepared with one or more monomers with at least one anionic group selected from the group consisting of carboxylic acids, sulfonic acids, sulfuric acids, sulfinic acids, phosphoric acids, phosphonic acids and phosphinic acids, and the corresponding salts thereof.

28. The lens of claim 1 comprising a refractive index of from 1.38 to 1.55.

29. The lens of claim 10 comprising a refractive index of from 1.38 to 1.55.

* * * * *